United States Patent
Pieczarek et al.

(10) Patent No.: US 9,964,502 B2
(45) Date of Patent: May 8, 2018

(54) THERMAL CONDUCTIVITY DETECTOR COMPRISING A SEALED CAVITY

(71) Applicant: Thermo Electron LED GmbH, Langenselbold (DE)

(72) Inventors: Waldemar Pieczarek, Langenselbold (DE); Carsten Krejtschi, Frankfurt (DE); Detlef Dornseiff, Allendorf (DE)

(73) Assignee: Thermo Electron LED GmbH, Langenselbold (DE)

( * ) Notice: Subject to any disclaimer, the term of this patent is extended or adjusted under 35 U.S.C. 154(b) by 76 days.

(21) Appl. No.: 14/466,473

(22) Filed: Aug. 22, 2014

(65) Prior Publication Data

US 2015/0052974 A1    Feb. 26, 2015

(30) Foreign Application Priority Data

Aug. 23, 2013 (DE) ........................ 10 2013 014 144

(51) Int. Cl.
*G01N 25/18*    (2006.01)
*G01N 30/66*    (2006.01)
*G08B 21/00*    (2006.01)

(52) U.S. Cl.
CPC ........ *G01N 25/18* (2013.01); *Y10T 29/49002* (2015.01)

(58) Field of Classification Search
CPC ...... G01N 25/18; G01N 27/18; G01N 27/121; G01N 30/66; Y10T 29/49002; G08B 21/00; H05B 6/6458

(Continued)

(56) References Cited

U.S. PATENT DOCUMENTS 3,676,771 A    7/1972    Loup et al.
4,059,366 A *  11/1977   Gannaway .............. F04B 49/10
                                                  417/32

(Continued)

FOREIGN PATENT DOCUMENTS

DE            1965462 A1     7/1970
DE     102011101503 A1    11/2012

(Continued)

OTHER PUBLICATIONS

Espacenet, English Machine Translation of European Application No. EP2163887A1, published on Mar. 17, 2010, retrieved from http://worldwide.espacenet.com on Jul. 29, 2014 (16 pages).

(Continued)

*Primary Examiner* — Manish S Shah
*Assistant Examiner* — Suman K Nath
(74) *Attorney, Agent, or Firm* — Wood Herron & Evans LLP

(57) ABSTRACT

The present invention relates to a thermal conductivity detector, comprising a sensor block having two cavities for the purpose of accommodating gases, wherein one of the cavities is open and the other cavity is sealed and in each of the cavities there is disposed a thermistor and also sealing elements for the purpose of sealing the cavities, which sealing elements comprise electric current feed through elements, which are electrically connected to the respective thermistor disposed in the respective cavity. At least the sealing element in the sealed cavity is a glass to metal feed through element, which is welded to the sensor block to form a gas-tight joint. The present invention further relates to a method for the production of the thermal conductivity detector.

25 Claims, 2 Drawing Sheets

(58) Field of Classification Search
USPC .................................. 73/25.03, 25.05, 866.5
See application file for complete search history.

(56) References Cited

U.S. PATENT DOCUMENTS

| | | | |
|---|---|---|---|
| 5,551,283 A | 9/1996 | Manaka et al. | |
| 5,876,765 A * | 3/1999 | Hinterlechner | B29C 45/14655 |
| | | | 264/272.17 |
| 2002/0149486 A1* | 10/2002 | Lee | H05B 6/6458 |
| | | | 340/602 |
| 2005/0006236 A1* | 1/2005 | Kim | G01N 27/18 |
| | | | 204/415 |
| 2005/0066707 A1* | 3/2005 | Katsuki | G01N 27/18 |
| | | | 73/23.21 |
| 2008/0143347 A1* | 6/2008 | Casey | G01N 33/2852 |
| | | | 324/663 |
| 2010/0186501 A1* | 7/2010 | Fink | G01K 1/143 |
| | | | 73/431 |
| 2010/0242573 A1* | 9/2010 | Matsuhama | G01N 25/18 |
| | | | 73/25.03 |
| 2011/0097503 A1* | 4/2011 | Shay | B05D 7/142 |
| | | | 427/435 |
| 2011/0148050 A1* | 6/2011 | Vissing | B05D 1/62 |
| | | | 277/650 |
| 2011/0305258 A1* | 12/2011 | Boutchich | G01J 5/12 |
| | | | 374/130 |
| 2012/0204623 A1* | 8/2012 | Matsuno | G01N 25/18 |
| | | | 73/25.03 |
| 2014/0069187 A1* | 3/2014 | Ranftl | G01K 13/02 |
| | | | 73/431 |

FOREIGN PATENT DOCUMENTS

| | | | | |
|---|---|---|---|---|
| EP | 2163887 A1 | 3/2010 | | |
| WO | WO 2012156057 A1 * | 11/2012 | ............ | G01K 13/02 |

OTHER PUBLICATIONS

Espacenet, English Machine Translation of German Application No. DE102011101503A1, published on Nov. 22, 2012, retrieved from http://worldwide.espacenet.com on Jul. 29, 2014 (11 pages).

* cited by examiner

THERMAL CONDUCTIVITY DETECTOR COMPRISING A SEALED CAVITY

CROSS-REFERENCE TO RELATED APPLICATIONS

The present application claims priority under 35 U.S.C. § 119 of German Patent Application No. 10 2013 014 144.3, filed Aug. 23, 2013, the disclosure of which is hereby incorporated herein by reference in its entirety.

FIELD OF THE INVENTION

The present invention relates to a thermal conductivity detector comprising a sealed cavity. The thermal conductivity detector is, for instance, used in laboratory equipment such as climatic cabinets, specifically, incubators or drying cabinets, or in gas chromatographs, more particularly, for the determination of variables such as humidity, gas content, or gas pressure. Additionally, the present invention relates to a method for the manufacture of such a thermal conductivity detector.

BACKGROUND OF THE INVENTION

Various forms of implementation of thermal conductivity detectors are known from the prior art. A prevalent form of thermal conductivity detectors is a thermal conductivity detector incorporating a Wheatstone bridge. The thermal conductivity detector comprises a stainless steel block, in which two separate cavities are formed, one of which contains a sample gas to be measured whereas the other contains a reference gas. A negative temperature coefficient resistor, that is, a thermistor, the resistance value of which varies depending on the temperature, is disposed in each of the cavities. The stainless steel block enclosing the cavities serves as heat coupling means between the two cavities and is usually kept at a constant temperature level that is below the temperature of the thermistor. The heat output, that is, the temperature of the respective negative temperature coefficient resistor or thermistor inside a cavity, depends on the heat conductivity "λ" of the respective gas located in each of the cavities. If the thermistors in the two cavities are interconnected in the manner of a Wheatstone bridge, the circuit will remain balanced as long as the composition of the gas in the reference cavity or the measuring cavity is the same or remains unchanged from the initial situation. Should the conductivity of the sample gas then change, for example, due to changes in the material composition of the gas in the measuring cavity, a change in temperature of the thermistor in the measuring cavity will occur and a voltage (bridge voltage) can be tapped between the two branches of the bridge. Variables such as gas content, gas pressure, humidity, etc., can thus be determined by means of the thermal conductivity detector. Such a thermal conductivity detector is, therefore, frequently used in lab environments, for example, in situations involving climatic cabinets, such as incubators, or gas chromatographs.

In order to maintain the measuring accuracy of the thermal conductivity detector, it is essential that the composition of the gas in the reference cavity remains constant throughout the measuring process. This may be achieved by a continuous flushing of the reference cavity with reference gas. This approach, however, is relatively complicated and expensive. An easier and less expensive approach is to hermetically seal the reference cavity after filling in the reference gas, so that there can be no exchange of gas and its composition remains unchanged. However, this is difficult to achieve in practice, since, on the one hand, a permanently gas-tight seal of the cavity is difficult to attain, especially when the thermal conductivity detector is used in a high temperature range. On the other hand, foreign substances can be released during the sealing of the cavity, or later during operation of the unit, inadvertently changing the gas composition in the cavity. Therefore, a drift is frequently observed, by means of which the readings on the thermal conductivity detector will become distorted over time.

It is, therefore, an object of the present invention to provide a thermal conductivity detector which has a sealed reference cavity, is easy to manufacture, and yet functions reliably and with the least possible drift over a long period of time, even at high ambient temperatures of up to 180° C. or higher.

SUMMARY OF THE INVENTION

According to a first aspect of the present invention, the present invention relates to a thermal conductivity detector. This thermal conductivity detector comprises a sensor block comprising two cavities for the accommodation of gas, a thermistor being located in each cavity. One cavity is open and the other cavity is sealed. Furthermore, sealing elements for sealing the cavities are present, which comprise means for current feed through, which are electrically connected to the respective thermistor disposed in each cavity. According to one embodiment of the present invention, at least the sealing element of the sealed cavity is a glass to metal feed through element that is welded to the sensor block to form a gas-tight seal therewith.

Thus, the thermal conductivity detector of the present invention differs from conventional ones in that a glass to metal feed through element is used to seal or close the sealed cavity. As described in the introduction, the sealed cavity serves to accommodate a reference gas, which is to be hermetically enclosed in the cavity such that its composition remains unchanged. Additionally, it is imperative that the composition of the reference gas does not change due to the intrusion of foreign materials into the cavity. All of these objectives are achieved in an ideal manner by the thermal conductivity detector according to the present invention. On the one hand, this is due to the use of the glass to metal feed through itself, which consists of materials that do not involve the risk of contamination of the reference gas, since, for example, virtually no outgassing takes place, even at high temperatures. On the other hand, the method of attaching and sealing the glass to metal feed through elements in the sensor block leads to a very stable and gas-tight configuration. Hardly any impurities that might adversely affect the composition of the reference gas are generated during the welding process. Gaseous impurities that may possibly enter the cavity during welding are of no concern, because the amount of these impurities is very slight, they are taken into consideration during the initial calibration of the thermal conductivity detector, and, therefore, do not interfere with the subsequent measuring procedure. Compared with other methods of production, the impurities resulting from welding the cavity are minimal.

Instead of welding the sealing element to the sensor block to seal the cavity, adhesive bonding, a combination of adhesive bonding and compressing, only compressing, screwing, or soldering might be employed. The individual connecting methods have different advantages and disadvantages, which have been examined in detail by the inventors of the present application.

Using an adhesive compound has been found to include the drawback that the adhesive used outgases over time, thus changing the composition of the gas in the closed cavity. An undesirable drift occurs. Furthermore, adhesives that are suitable for high temperatures such as 180° C. or more may have long drying times and may need to be heated in order to cure. Upon heating, however, the existing gas in the cavity expands and often causes a leak in the adhesive bond.

In the case of adhesive bonding combined with compression, a small pressure equalization hole is provided which is closed by compression following the application of adhesive and the subsequent introduction of reference gas. Here again, there is still the problem of outgassing occurring on account of the use of an adhesive compound, as a result of which the gas composition within the cavity changes, leading to drift and lack of accuracy. A further drawback results from the necessity of a further procedural step during the manufacture of a thermal conductivity detector consisting of the required act of compression.

It has been found that when use is made of screws, the screw thread is not sufficient as a seal. Therefore, additional seals are required. These may not outgas or become brittle when used over long periods of time and at the specified operational temperature range of up to 180° C. or above. If a glass feed through electrode is combined with a screw joint, a defined torque is necessary to ensure that the glass seal is not broken. Within a range of experiments, special screws with glass feed through elements for attaching sensors were manufactured and tested in several versions. It was found that it is very difficult to achieve sufficient process reliability. Naturally, the screws may not loosen.

In the case of soldering, flux residues can enter the cavity and change the gas composition. This results in an undesirable signal drift.

Using compression as a sealing method was ultimately found to be a difficult process to optimize, since it is necessary to ensure that the glass seal of the sensor joints will not crack. The process requires flanges that are quite elaborate to manufacture. Furthermore, the force of compression must be high enough to withstand the increase in pressure at high temperatures.

Therefore, among the examined joining and sealing methods, only the process of welding a glass to metal feed through element to the sensor block has been found to be a useful method for sealing a cavity quickly and securely using a sealing element having an electrical current feed through element and for creating a thermal conductivity detector showing very low drift even at high temperatures.

According to one embodiment of the present invention, at least the sealing element used for the sealed (reference) cavity is a glass to metal feed through element. Such glass to metal feed through elements are known in the prior art, and in principle, such conventional feed through elements may be used within the scope of the present invention. Typically, a glass to metal feed through element consists of a metallic outer part, a pre-molded glass part, and one or more inner conductors (current feed through element) enclosed therein. These components are hermetically sealed under a protective gas atmosphere by using a special thermal process at approx. 1000° C., for example. In the case of a so-called "matched" glass feed through element, the hermetically sealed join between the glass and the metal is achieved by means of oxide layers. The components used have approximately the same coefficients of thermal expansion. In the case of a compression glass feed through element, the outer metal part, typically of steel or stainless steel, has a much higher coefficient of thermal expansion than the glass and inner conductors. The hermetically sealed join is achieved by compression. Nowadays, the glass to metal feed through elements described are standard components, and using them to manufacture a thermal conductivity detector according to the present invention simplifies and cheapens the manufacture thereof. Preferably, matched glass feed through elements are used for the present invention, because they have very good sealing properties, even at varying or high ambient temperatures, due to the similar coefficients of thermal expansion of the materials.

A glass to metal sealing element is preferably used, not only to seal the closed cavity, but also the open one, where it is likewise sealed by welding. The open cavity is formed in known manner such that a sample gas can flow therethrough. It is, therefore, closed by the sealing element on one side only, while advantageously the other side remains open and serves as a gas inlet and outlet.

Apart from the use of at least one sealing element in the form of a glass to metal feed through element and its mounting in the sensor block, the thermal conductivity detector according to the present invention, as already described, does not differ from conventional thermal conductivity detectors. The sensor block is preferably a metallic block, more preferably, a stainless steel block. The sensor block provides heat coupling means for the two cavities and forms a heat sink. The cavities are preferably in the form of bores, whereas the sealed cavity is advantageously in the form of a blind-hole bore, and the open cavity is in the form of a through bore in the sensor block. It is preferred that the two bores are formed so as to be parallel to each other, advantageously arranged symmetrically in the sensor block. The open and sealed cavities have, for reasons of simplicity of production, preferably identical, and, in particular, circular, cross-sections. However, any other elongated, cross-sections can be used. There may be exactly two cavities formed in the sensor block, but there may also be more than two cavities, for example, four cavities. In the case of four cavities, these may consist of, for example, two open and two closed cavities. The sensor block itself may consist of a single part or multiple parts. According to a preferred embodiment, the sensor block is substantially cylindrical, since such a shape can be manufactured in a particularly simple manner.

Each cavity contains a thermistor. According to the present invention, a thermistor is understood to be a variable electrical resistor, whose resistance value varies, reproducibly, with changes in temperature. The thermistor is conventionally electrically connected, for example, by means of wires, to the electrical feed through elements in the sealing member, which makes it possible to feed electric current or voltage to the thermistor from an external source. A welding process, in particular, a laser welding process, may advantageously be used for forming the joint. When arranged in pairs, these thermistors are advantageously interconnected to form a Wheatstone bridge circuit via electrical feed through elements, as is known per se in the prior art.

According to one embodiment of the present invention, a welding process is used, at least for the closed cavity, for the purpose of sealing the sealing element. Basically, any suitable welding process, for example, resistance welding or cold welding, may be used in this case. Preferably, however, a laser welding method is used to form a laser welded joint. The advantage of such a welded joint resides in the fast and reliable process leading to permanently sealed joints, and in the short production time, which is considerably reduced as compared with the long curing times involved in gluing. The welding procedure takes a maximum of 5 minutes, which, compared with the curing time for glue (about 12 to 24 hours), constitutes an enormous reduction in installation time. In addition, only a single step is required, which proves to be beneficial compared with the two-step procedures involving subsequent compression. Within the scope of the present invention, it is basically possible to follow up the welding step with a compression step. A sealing element equipped with an equalizing port may alternatively first be welded to the cavity. In this way, the reference gas may be filled into the cavity after welding, following which the equalizing port is closed by compression. This would allow impurities that have entered the cavity during welding to be flushed out by means of the reference gas and, thus, removed from the cavity before it is permanently sealed. However, the additional process step and the slightly lower gas tightness achieved for the cavity would be a disadvantage. Moreover, such an additional step is generally not necessary, as only very small amounts of impurities enter the cavity during welding. These impurities, however, are irrelevant since any deviations caused thereby can be taken into consideration and compensated for during calibration of the thermal conductivity detector.

The gas tightness of the sealed cavity in the thermal conductivity detector according to the present invention is of particular importance. There is basically no risk of the open cavity becoming leaky at high temperatures due to the resulting increase in pressure, or of the composition of the gas filled into the open cavity changing. It is nevertheless preferable, according to one embodiment of the present invention, to use a sealing element for the open cavity that is of the same type as the one used for the sealed cavity, that is to say, a glass to metal through feed element, likewise attached by welding. However, this has mainly practical reasons, since the same parts can be processed in the same manner, which then simplifies handling and installation procedures. In addition, the use of the same elements in the reference and measuring cells simplifies collation of the readings and increases the accuracy of the measurements. Another benefit is that the gases (reference gas or sample gas) exclusively comes into contact with glass or metallic materials in the cavities, and even at high temperatures there is no risk of the gases being contaminated by products of evaporation or decomposition, nor of the readings being falsified.

The at least one sealing element is preferably shaped such that it can be inserted positively, that is to say, in a form-fitting manner, into the corresponding cavity. This means that the sealing element bears as closely as possible, at least over a part of its overall outer height, against the wall of the cavity, such that only a very small gap remains between the sealing element and the sensor block. This gap is closed by means of welding so that no gas can pass therethrough. It is possible, for example, to engulf the sealing element completely in the cavity and either form the seam at the top edge region of the cavity, if the surface of the sealing element is located below the surface of the sensor block within the cavity, or on the surface of the sensor block, if the sealing element is flush with the surface of the sensor block. Parts of the sealing element may alternatively protrude above the surface of the sensor block. In this case, it is preferable to provide a flange at the upper end of the sealing element, which flange protrudes laterally beyond the periphery of the remaining sealing element and rests on the surface of the sensor block when the sealing element has been inserted into the cavity. The welded seam is then generated, of course, at the outer edge of the flange.

The commonly used sensor blocks, and the materials used as the exterior materials of the glass to metal feed through elements, are usually made of stainless steel and, thus, make it possible to carry out welding thereon without making any special modifications or special selections. In certain cases, however, especially when a laser welding method is used to weld the sensor block and the glass to metal feed through element, the properties of the materials to be welded need to be selected and matched accordingly. According to one embodiment of the present invention, it is preferred to use a sensor block that is made entirely, or at least in the region of the welded joint, of stainless steel. Among such stainless steels, chromium nickel steels and those of the type 1.4301 (X5CrNi18-10, ASTM 304) are particularly preferred. As regards the sealing element, more specifically, the glass to metal feed through element, stainless steel, preferably a chromium nickel molybdenum steel and, more particularly, one of the class 1.4404 (X2CrNiMo17-12-2, ASTM 316L), is used at least in the region of the welded seam. The metal "Kovar" (an iron nickel cobalt alloy) commonly used for glass to metal feed through elements is very difficult to weld to stainless steel, for which reason this conventional type of glass to metal feed through element should not be used for laser-welded joints.

According to one embodiment of the present invention, NTC thermistors and PTC thermistors may basically be used. According to a preferred embodiment of the present invention, the thermistor is a PTC thermistor showing a higher conductivity at low temperatures than at high temperatures. Basically, PTC thermistors include all metals. PTC thermistors, when used as electronic components, are often manufactured from semiconductive polycrystalline ceramics (such as barium titanate), which over a certain temperature range establish a barrier at the grain boundary. There are also silicon based PTC thermistors.

NTC thermistors, on the other hand, include pure semi-conductor materials, compound semi-conductors and various other alloys. With an NTC thermistor, the characteristics of the material depend to a high degree, due to the underlying semi-conductor effect, on defects, including the doping of the base material. The processing operations (mixing, grinding, pressing, sintering) have a great effect on the properties and the long-term stability of NTC thermistors. Therefore, for a long time, NTC thermistors could only be manufactured having very different characteristics from batch to batch and were less suitable for accurate temperature measurements. With each replacement, it was necessary to perform a re-calibration. For this reason, it is beneficial, according to the present invention, not only NTC thermistors, but also more reliable and cheaper PTC thermistors can be used.

In one embodiment of the present invention, the PTC thermistor is a Pt100 thermistor. A Pt100 thermistor is a platinum temperature sensor or platinum resistor whose nominal resistance Ro at a temperature of 0° C. equals 100Ω. The Pt100 is used on a broad scale industrially and is, therefore, a standard component. The Pt100 shows very good long-term stability compared with conventional NTC thermistors. The use of a Pt100, therefore, has a positive effect on the durability of the overall thermal conductivity detector and serves to optimize the drift, that is to say, to reduce the drift. In addition, the cost of the thermal conductivity detector can be reduced. The connection between the electric current feed through elements in the sealing elements and the thermistor can be made in any conventional manner, for example, by means of electrically conducting wires.

According to one embodiment of the present invention, the open cavity exhibits a sample gas and the closed cavity a reference gas. The reference gas has a substantially known composition, which virtually does not change over time. The sample gas is a gas to be analyzed, which flows through the open cavity. In order to protect the open cavity from contamination, the gas inlet may be closed in conventional manner with a gas-permeable filter, for example, a sintered filter.

According to a further aspect, the present invention relates to the use of the thermal conductivity detector to ascertain the content of a component in a gas mixture, more particularly, the $CO_2$ content of the air, or to ascertain humidity or a gas pressure. In particular, the thermal conductivity detector can be used to ascertain these variables in the interior of a gas chromatograph, an incubator, more particularly, a $CO_2$ incubator, a drying cabinet, or a vacuum drying cabinet, as used in laboratories. The high temperature prevailing in these devices, either in normal operation or during the disinfection process, and/or the high degree of humidity, place particularly high demands on the temperature resistance and durability of the thermal conductivity detectors used therein. Basically, the determination of the above variables is carried out by means of the thermal conductivity detector of the present invention as in the prior art. The said variables are indirectly inferred from the measured thermal conductivity.

According to a further aspect, the present invention relates to a gas chromatograph comprising a thermal conductivity detector of the type described in greater detail above. In this case, the gas to be analyzed coming from the gas chromatograph is passed through the open cavity of the thermal conductivity detector.

A further aspect of the present invention relates to a method of manufacturing the thermal conductivity detector of the present invention. The method of the present invention comprises at least the following steps:

providing a sensor block with an open cavity and a closed cavity;

providing a thermistor having connecting means;

providing a sealing element containing an electric current feed through element in the form of a glass to metal feed through element;

connecting the thermistors to the electric current feed through elements; and welding, particularly by means of laser welding, of the sealing element to the sensor block for the purpose of producing a gas-tight seal of the closed cavity.

BRIEF DESCRIPTION OF THE DRAWINGS

The present invention is further described below with reference to drawings. In the purely diagrammatic drawings, which only describe a preferred example of the present invention, without the present invention being restricted thereto, like reference symbols denote like parts. More specifically, in these drawings.

DETAILED DESCRIPTION OF THE INVENTION

Figures 1A, 1B:
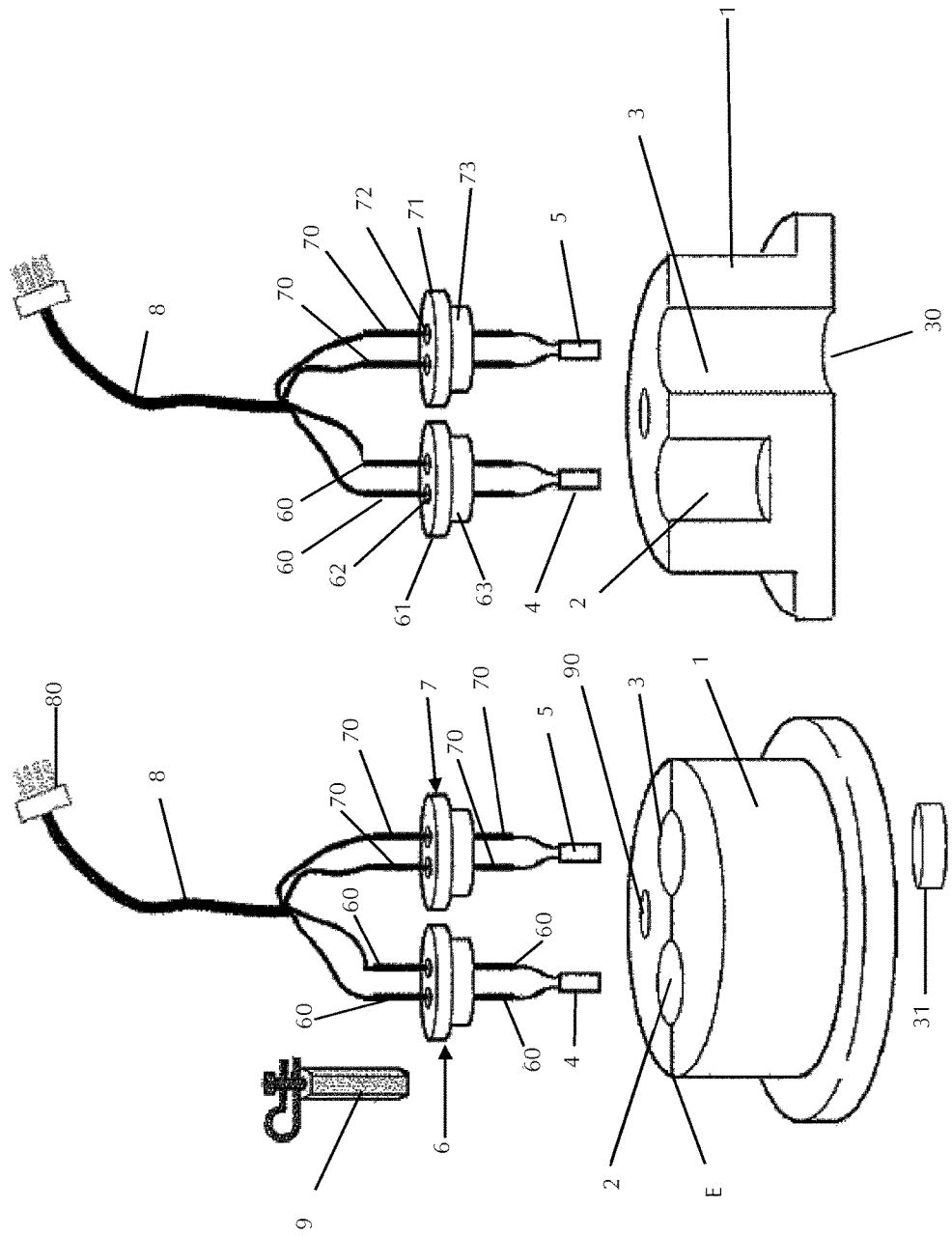
FIG. 1(a) is a perspective view of a thermal conductivity detector according to one embodiment of the present invention in exploded view.
FIG. 1(b) is a cross-sectional view of the sensor block of the thermal conductivity detector shown in FIG. 1(a)

FIG. 1 illustrates the basic structure of a thermal conductivity detector according to one embodiment of the present invention. In the example shown, the thermal conductivity detector has a sensor block 1 made of stainless steel, for example, of type 1.4301. It is substantially cylindrical in shape. Two cavities are formed on the center dividing plane E of the sensor block, which are also divided centrally by the plane E. The cavities 2, 3 show a circular cross-section of equal diameter. The cavity 2 is designed in the form of a blind hole and is closed at the bottom. The cavity 3 is an open cavity, which is designed as a through bore through the sensor block 1. This is particularly seen in FIG. 1(b), which shows a cross-section of the sensor block taken along the plane E.

In the cavities 2 and 3, there are inserted sealing elements 6, 7 respectively. FIGS. 1(a) and 1(b) show the parts to be inserted into the sensor block cavities in an unassembled state. The sealing elements 6, 7 according to the present invention are glass to metal feed through elements. They exhibit an outer metal part having two through bores, each of which a glass part 62, 72 is melted into, which in turn tightly encloses a respective electrical feed through element 60, 70. The ends protruding into the interior of the cavities 2, 3 of the electrical feed through elements 60 or 70 are each electrically connected by means of wires to a thermistor 4 or 5, respectively. The thermistors 4, 5 are, in this case, Pt100 thermistors. On the outside, the electrical feed through elements 60, 70 of the sealing elements 6, 7 are connected via wire 8 to a connector plug 80, through which the thermal conductivity detector can be connected to a power source. The holder 9 serves to secure the wire 8 and is inserted into the cavity 90 in the sensor block.

Figure 2:
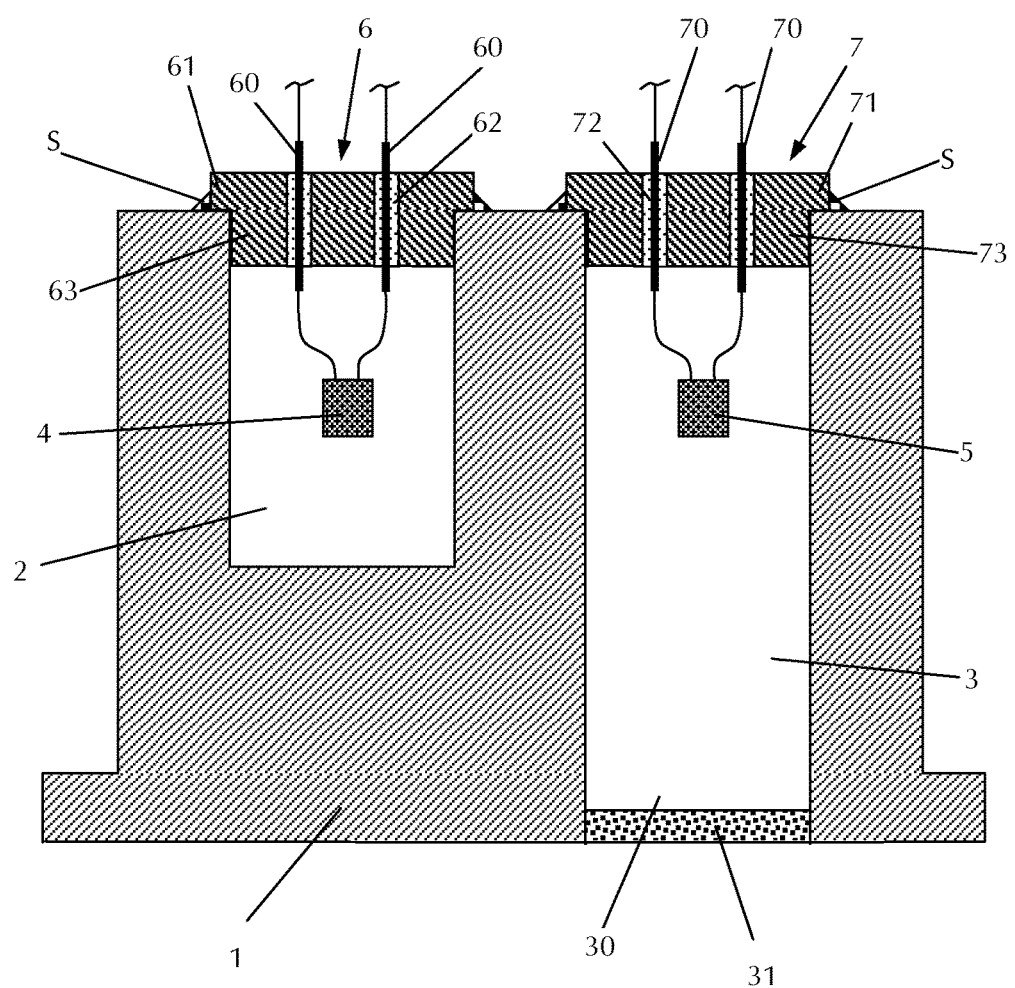
FIG. 2 is a cross section of the thermal conductivity detector.

FIG. 2 shows the thermal conductivity detector in its assembled state as a cross-section taken along the plane E. The thermistors 4 and 5 are shown in the assembled state within the cavities 2 and 3, respectively. The sealing elements 6 and 7 bear against the sensor block 1. Flanges 61, 71 of the metallic outer parts of the sealing element 6, 7 respectively rest against the surface of the sensor block 1. The regions 63, 73 adjoining the flanges 61, 71 are disposed such that their smaller diameter fits in the cavities with their outer circumference at the smallest possible distance from the walls of the cavities 2, 3. The outer metal part of the sealing elements 6, 7 comprising the flange 61, 71 and main part 63, 73 is preferably made of stainless steel of the type 1.4404. This allows for the material of the outer part of the sealing elements 6, 7 to be welded to the material of the sensor block 1. For this purpose, a laser welding method is preferably used. The welded joint S is advantageously generated at the edge of the flanges 61, 71 in such a manner that the welded joint S extends completely around the edge of the flange and, thus, results in a gas-tight seal between the flange and the sensor block. The gas-tightness achieved is sufficiently high for the gas enclosed in the cavity 2 not to leak out of the cavity even when the thermal conductivity detector is exposed to very high temperatures, for example, of about 180° C. during a high-temperature disinfection stage of an incubator. The open cavity 3, on the other hand, does not possess gas-tightness, but allows the entry of a sample gas through the gas inlet port 30, even if a filter 31, such as a sintered filter, has been installed for protection against contamination.

While the present invention has been illustrated by description of various embodiments and while those embodiments have been described in considerable detail, it is not the intention of Applicants to restrict or in any way limit the scope of the appended claims to such details. Additional advantages and modifications will readily appear to those skilled in the art. The present invention in its broader aspects is therefore not limited to the specific details and illustrative examples shown and described. Accordingly, departures may be made from such details without departing from the spirit or scope of Applicants' invention.

What is claimed is:

1. A thermal conductivity detector, comprising:
   a sensor block comprising:
      first and second cavities for the accommodation of gases, each of the first and second cavities having a respective opening at a respective one end of the first and second cavities, with the first cavity having a closed bottom and the second cavity being open at respective ends of the first and second cavities opposite the respective openings at the respective one end of the first and second cavities;
      a discrete first sealing element and a discrete second sealing element closing the respective openings at the respective one end of the first and second cavities, with the first cavity accommodating a reference gas; and;
      a thermistor disposed in each of the respective first and second cavities, said first and second sealing elements each comprising electric current feed through elements that are connected to the thermistor disposed in each of the respective first and second cavities,
   wherein at least the first sealing element is a glass to metal feed through element having a metallic outer part which is welded to the sensor block at a weld joint (S) to form a gas-tight joint therewith so as to entirely close the first cavity.

2. The thermal conductivity detector according to claim 1, wherein the first sealing element in the first cavity is a glass to metal feed through element that is welded to said sensor block to form a gas-tight joint therewith.

3. The thermal conductivity detector according to claim 1, wherein at least one of the first and second sealing elements is positively fitted into at least one of respective first and second cavities.

4. The thermal conductivity detector according to claim 1, wherein at least one of the first and second sealing elements comprises a flange that rests on a marginal region surrounding at least one of first and second cavities in said sensor block and is welded to said sensor block.

5. The thermal conductivity detector according to claim 4, wherein the flange is welded to said sensor block in the region of said flange.

6. The thermal conductivity detector according to claim 1, in which the sensor block comprises, at least in the region of said welded joint (S), stainless steel.

7. The thermal conductivity detector according to claim 6, wherein the sensor block comprises entirely stainless steel.

8. The thermal conductivity detector according to claim 6, wherein the sensor block comprises, at least in the region of said weld joint (S), a chromium nickel steel.

9. The thermal conductivity detector according to claim 6, wherein the sensor block comprises, at least in the region of said weld joint (S), a steel of the type 1.4301.

10. The thermal conductivity detector according to claim 1, wherein at least one of said sealing elements comprises, at least in the region of the first and second welded joint (S), stainless steel.

11. The thermal conductivity detector according to claim 10, wherein the at least one sealing element comprises, at least in the region of said weld joint (S), a chromium nickel molybdenum steel.

12. The thermal conductivity detector according to claim 10, wherein the at least one sealing element comprises, at least in the region of said weld joint (S), a steel of the type 1.4404.

13. The thermal conductivity detector according to claim 1, wherein said welded joint (S) is a laser welded joint.

14. The thermal conductivity detector according to claim 1, wherein the thermistor is a PTC thermistor.

15. The thermal conductivity detector according to claim 14, wherein said PTC thermistor comprises a Pt100-thermistor.

16. The thermal conductivity detector according to claim 1, wherein said first cavity is in the form of a blind hole in said sensor block and said second cavity is in the form of a hole passing through the sensor block.

17. The thermal conductivity detector according to claim 16, wherein said sealed cavity and said open cavity are parallel to each other.

18. The thermal conductivity detector according to claim 1, wherein said second cavity comprises a filter disposed across a gas inlet of said open cavity.

19. The thermal conductivity detector according to claim 18, wherein said filter comprises a sintered filter.

20. The thermal conductivity detector according to claim 1, wherein a reference gas is enclosed in the sealed first cavity.

21. The use of the thermal conductivity detector according to claim 1, for the purpose of determining the content of a component in a gas mixture.

22. The use of the thermal conductivity detector according to claim 21, for the purpose of determining one of a $CO_2$ content in air, an air humidity and a gas pressure.

23. A method for the fabrication of a thermal conductivity detector according to claim 1, comprising the steps of:
   providing a sensor block comprising a first, sealed cavity and a second, open cavity;
   providing a thermistor;
   providing an electric current feed through element in a sealing element in the form of a glass to metal feed through element;
   connecting said thermistor to said electric current feed through element; and
   welding the sealing element to said sensor block for the purpose of forming said gas-tight seal of said sealed cavity.

24. The method according to claim 23, wherein the welding step comprises laser welding.

25. The use of the thermal conductivity detector according to claim 1 inside an internal chamber of a climatic cabinet.

* * * * *